US012678437B2

(12) United States Patent
Jung et al.

(10) Patent No.: US 12,678,437 B2
(45) Date of Patent: Jul. 14, 2026

(54) USE OF Cyclo-HisPro (CHP) FOR LOWERING BLOOD PRESSURE

(71) Applicants: NOVMETAPHARMA CO., LTD., Seoul (KR); SEOUL NATIONAL UNIVERSITY HOSPITAL, Seoul (KR); SEOUL NATIONAL UNIVERSITY R&DB FOUNDATION, Seoul (KR)

(72) Inventors: Hoe Yune Jung, Pohang-si (KR); Heon Jong Lee, Incheon (KR); Yon Su Kim, Seoul (KR); Seung Hee Yang, Seoul (KR)

(73) Assignees: NOVMETAPHARMA CO., LTD., Seoul (KR); SEOUL NATIONAL UNIVERSITY HOSPITAL, Seoul (KR); SEOUL NATIONAL UNIVERSITY R & DB FOUNDATION, Seoul (KR)

( * ) Notice: Subject to any disclaimer, the term of this patent is extended or adjusted under 35 U.S.C. 154(b) by 696 days.

(21) Appl. No.: 17/912,942

(22) PCT Filed: Mar. 19, 2021

(86) PCT No.: PCT/KR2021/003424
§ 371 (c)(1),
(2) Date: Sep. 20, 2022

(87) PCT Pub. No.: WO2021/187942
PCT Pub. Date: Sep. 23, 2021

(65) Prior Publication Data
US 2023/0165855 A1 Jun. 1, 2023

(30) Foreign Application Priority Data

Mar. 20, 2020 (KR) ........................ 10-2020-0034625

(51) Int. Cl.
*A61K 31/4985* (2006.01)
*A61P 9/12* (2006.01)

(52) U.S. Cl.
CPC ............ *A61K 31/4985* (2013.01); *A61P 9/12* (2018.01)

(58) Field of Classification Search
CPC .............................. A61K 31/4985; A61P 9/12
See application file for complete search history.

(56) References Cited

U.S. PATENT DOCUMENTS

2004/0185125 A1 9/2004 Song
2008/0242621 A1 10/2008 Suh

FOREIGN PATENT DOCUMENTS

CN 107922458 A 4/2018
EP 1 442 741 A1 8/2004
(Continued)

OTHER PUBLICATIONS

Cohen, Curr Cardiol Rep 19, 98 (2017) (Year: 2017).*
(Continued)

*Primary Examiner* — San Ming R Hui
(74) *Attorney, Agent, or Firm* — Sughrue Mion, PLLC

(57) ABSTRACT

New uses of Cyclo-HisPro (CHP) or a salt thereof for lowering blood pressure are disclosed. More specifically, the present invention relates to a pharmaceutical composition for lowering blood pressure, containing CHP or a salt thereof, and a functional health food composition containing CHP or a salt thereof; a method for lowering blood pressure using CHP or a salt thereof; a use of CHP or a salt thereof in the manufacture of antihypertensive agents; a pharmaceutical composition or a functional health food, for preventing or treating hypertension or complications thereof, containing CHP or a salt thereof; a method for preventing or treating hypertension or complications thereof by using CHP
(Continued)

or a salt thereof; and a use of CHP or a salt thereof in the manufacture of a medicament for preventing or treating hypertension or complications thereof.

3 Claims, 7 Drawing Sheets

Specification includes a Sequence Listing.

(56)                    References Cited

FOREIGN PATENT DOCUMENTS

| EP | 3 486 252 | A1 | 5/2019 |
| KR | 10-2012-0089970 | A | 8/2012 |
| KR | 10-2013-0006170 | A | 1/2013 |
| KR | 10-2014-0101974 | A | 8/2014 |
| KR | 10-2018-0008305 | A | 1/2018 |
| KR | 10-2019-0074746 | A | 6/2019 |
| KR | 10-2133151 | B1 | 7/2020 |
| KR | 10-2140910 | B1 | 8/2020 |

OTHER PUBLICATIONS

Kailas S Khomane, et al., "Novel thyrotropin-releasing hormone analogs: a patent review", Expert Opin. Ther. Patents, 2011, vol. 21, No. 11, pp. 1673-1691 (19 pages total).

Silvia I. García, et al., "Thyrotropin-releasing hormone in cardiovascular pathophysiology", Regulatory Peptides, 2005, vol. 128, pp. 239-246 (8 pages total).

Lars-Owe D. Koskinen, "Effect of low intravenous doses of TRH, acid-TRH and cyclo(His-Pro) on cerebral and peripheral blood flows", Br. J. Pharmac., 1986, vol. 87, pp. 509-519 (11 pages total).

A. Minelli, et al., "Focus on cyclo(His-Pro): history and perspectives as antioxidant peptide", Amino Acids, 2008, vol. 35, pp. 283-289 (7 pages total).

Moon K. Song et al., "Anti-Hyperglycemic Activity of Zinc Plus Cyclo (His-Pro) in Genetically Diabetic Goto-Kakizaki and Aged Rats", Experimental Biology and Medicine, 2003, vol. 228, No. 11, pp. 1338-1345 (8 pages total).

Extended European Search Report issued Feb. 27, 2024 in European Application No. 21770955.9.

Elena Kaschina et al., "Angiotensin AT1/AT2 Receptors: Regulation, Signalling and Function", Blood Pressure, 2003, pp. 70-88, vol. 12.

Thu H. Le et al., "Physiological Impact of Increased Expression of the $AT_1$ Angiotensin Receptor", Hypertension, Oct. 2003, pp. 507-514, vol. 42.

Ulrich Förstermann et al., "Endothelial Nitric Oxide Synthase in Vascular Disease: From Marvel to Menace", Circulation, 2006, pp. 1708-1714, vol. 113.

Jinqiang Zhu et al., "Endothelial nitric oxide synthase: a potential therapeutic target for cerebrovascular diseases", Molecular Brain, 2016, pp. 1-8, vol. 9, No. 30.

International Search Report for PCT/KR2021/003424 dated Jul. 1, 2021.

Reisin, E., et al. ,"Failure of Cyclo (His-Pro) to Exhibit Natriuretic Activity," Neuropeptides, vol. 6, 1985, pp. 569-572 (4 pages total).

Korean Office Action issued Jun. 7, 2023 in KR Application No. 10-2021-0036268.

Communication dated Jul. 16, 2025 in European Application No. 21 770 955.9.

Landsberg, "Diet, Obesity and Hypertension: An Hypothesis Involving Insulin, the Sympathetic Nervous System, and Adaptive Thermogenesis", Quarterly Journal of Medicine, Dec. 1986, vol. 61, No. 236, pp. 1081-1090 (10 pages).

Troisi, et al., "Relation of Obesity and Diet to Sympathetic Nervous System Activity", Hypertension, May 1991, vol. 17, No. 5, pp. 669-677 (9 pages).

Communication dated Dec. 24, 2025 issued by the State Intellectual Property Office of the P.R.China in application No. 202180022746. 0.

* cited by examiner

1

USE OF Cyclo-HisPro (CHP) FOR LOWERING BLOOD PRESSURE

CROSS REFERENCE TO RELATED APPLICATIONS

This application is a National Stage of International Application No. PCT/KR2021/003424 filed Mar. 19, 2021, claiming priority based on Korean Patent Application No. 10-2020-0034625 filed Mar. 20, 2020.

INCORPORATION BY REFERENCE OF SEQUENCE LISTING

The content of the electronically submitted sequence listing, file name: Sequence_Listing_As_Filed.txt; size: 1,176 bytes; and date of creation: Sep. 19, 2022, filed herewith, is incorporated herein by reference in its entirety.

TECHNICAL FIELD

The present invention relates to a use of Cyclo-HisPro (CHP) for lowering blood pressure. More specifically, the present invention relates to a pharmaceutical composition for lowering blood pressure, including CHP, and a functional health food composition including the same; a method for lowering blood pressure using CHP; a use of CHP in the manufacture of antihypertensive agents; a pharmaceutical composition for preventing or treating hypertension or complications thereof, including CHP, and a functional health food composition including the same, for preventing or improving hypertension or complications thereof; a method for preventing or treating hypertension or complications thereof by using CHP; and a use of CHP in the manufacture of a medicament for preventing or treating hypertension or complications thereof.

BACKGROUND ART

Recently, the nutritional status has been dramatically improved due to economic growth, the improvement of the educational level and the development of science, and the diseases caused by changes in various life patterns including diet and the extension of life expectancy are also showing a tendency to diversify.

Cerebrovascular disease, which is highlighted as the leading cause of death after cancer in Korea, is due to the high incidence of hyperlipidemia and hypertension, In particular, high blood pressure is a major cause of complications such as cerebrovascular disease and cardiovascular disease, and it is showing an increasing trend as the diet is westernized and aging progresses.

The number of patients with renal impairment is also showing a gradual increase, and the causes thereof include an increase in diabetic nephropathy due to a change in living environment, an aging population or an increase in diabetic patients. The number of patients who develop kidney failure due to renal dysfunction or have no choice but to introduce dialysis is increasing every year, and in the case of dialysis therapy, side effects such as impaired red blood cell production, complications due to microglobulin accumulation and increased cardiovascular lesions have become problematic. In addition to coercive therapy, drugs that suppress the rise of blood electrolytes and a low-protein diet are prescribed for patients with renal failure, and in the case of renal anemia, erythropoietin is administered, but these are not considered to be sufficient to stop the progression of the condition. Renal diseases such as nephritis, diabetic nephropathy and renal failure often accompany high blood pressure, and in addition, hypertension is considered as one of the exacerbation factors of kidney disease, and antihypertensive agents which are expected to suppress the progression of kidney disease are also administered.

Although drugs for the treatment of hypertension include calcium channel blockers, diuretics, angiotensin-converting enzyme inhibitors and the like, antihypertensive drugs manufactured through chemical synthesis had problems due to side effects such as headache, liver disease, hot flashes, atrioventricular block and gout. In order to solve these problems, research for preventing and treating hypertension by using natural substances has been continued in recent years.

One of the most well-known models of hypertension in cells is the angiotensin II (AngII) model. AngII binds with angiotensin receptors present in blood vessels and performs various actions, and among them, AT1 (AT1R), which is a type 1 receptor, induces vasoconstriction, and AT2 (AT2R), which is a type 2 receptor, relaxes blood vessels to perform the opposite action as AT1 (Elena Kaschina & Thomas Unger, *Blood Press,* 12(2), 70-88, 2003). In fact, high blood pressure appears in patients with hypertension because the blood AngII concentration is maintained to be high or AT1 is expressed more strongly than AT2, and blood vessels are more likely to remain constricted rather than relaxed. Therefore, drugs that reduce the expression level of AT1 or blockers that block the binding of AngII to the AT1 receptor can be used as therapeutic agents for hypertension (Le T H, et al. *Hypertension,* 42(4), 507-514, 2003).

Arteriosclerosis, peripheral blood circulation disorder, vascular stenosis, cerebral infarction, angina pectoris, myocardial infarction and ischemic brain disease, as well as hypertension, are diseases caused by vasoconstriction, and vasoconstriction refers to a phenomenon in which blood vessels such as arteries including the aorta or veins are narrowed as the walls of blood vessels contract. For smooth blood circulation, blood flow in blood vessels must be increased, and the increase in blood flow requires the expansion of blood vessels. For vasodilation, nitric oxide (NO) is involved by the action of endothelial nitric oxide synthase (eNOS), which is a nitric oxide synthase of vascular endothelial cells (Ulrich Forstermann & Thomas Munzel, *Circulation,* 113, 1708-1714, 2006). In fact, for hypertension, NO production is reduced. In general, vascular smooth muscle is affected by several factors, and the cGMP signaling pathway of vascular smooth muscle cells by NO produced and secreted by vascular endothelial cells is a very important pathway in vascular relaxation (Zhu J, et, al., *Mol Brain,* 9, 20, 2016). NO is produced from L-arginine by eNOS in vascular endothelial cells. NO secreted from vascular endothelial cells flows into vascular smooth muscle cells, activates soluble guanylyl cyclase (sGC) and regulates blood pressure by relaxing vascular smooth muscle through a signal transduction system that increases the production of cGMP. Therefore, the NO production promoter can also be used as a therapeutic agent for hypertension.

Meanwhile, "Cyclo-HisPro (CHP)" is a naturally occurring circular dipeptide composed of histidine-proline, which is a metabolite of thyrotropin-releasing hormone (TRH) or a physiologically active dipeptide that is also synthesized in the body de novo through the metabolic process of TRH, and although the glycemic control effect thereof (Korean Patent Application No. 10-2013-0006170), the fibrosis treatment effect thereof (Korean Registered Patent No. 10-2140910) and the peritoneal fibrosis treatment effect thereof (Korean Registered Patent No. 10-2133151) have been disclosed, the blood pressure lowering effect of CHP is not known.

DISCLOSURE

Technical Problem

Under this background, the inventors of the present invention completed the present invention by confirming that Cyclo-HisPro (CHP) exhibited a blood pressure lowering effect in vascular endothelial cells through a decrease in the expression of angiotensin II type I receptor gene or protein; an increase in the expression of angiotensin II type II receptor gene or protein; an increase in the expression of VE-cadherin gene or protein; an increase in the expression of eNOS gene or protein; and/or increased NO production.

Accordingly, an object of the present invention is to provide a pharmaceutical composition for lowering blood pressure, including Cyclo-HisPro or a pharmaceutically acceptable salt thereof.

Another object of the present invention is to provide a health functional food composition for lowering blood pressure, including Cyclo-HisPro or a sitologically acceptable salt thereof.

Still another object of the present invention is to provide a method for lowering blood pressure by using Cyclo-HisPro or a pharmaceutically acceptable salt thereof.

Still another object of the present invention is to provide a use of Cyclo-HisPro or a pharmaceutically acceptable salt thereof in the manufacture of an antihypertensive agent.

Furthermore, an object of the present invention is to provide a pharmaceutical composition for preventing or treating hypertension or a complication thereof, including Cyclo-HisPro or a pharmaceutically acceptable salt thereof.

Another object of the present invention is to provide a health functional food composition for preventing or ameliorating hypertension or a complication thereof, including Cyclo-HisPro or a sitologically acceptable salt thereof.

Still another object of the present invention is to provide a method for preventing or treating hypertension or a complication thereof by using Cyclo-HisPro or a pharmaceutically acceptable salt thereof.

Still another object of the present invention is to provide a use of Cyclo-HisPro or a pharmaceutically acceptable salt thereof in the manufacture of a medicament for preventing or treating hypertension or a complication thereof.

Technical Solution

In order to solve the aforementioned problems, according to a first aspect, the present invention provides a pharmaceutical composition for lowering blood pressure, including Cyclo-HisPro or a pharmaceutically acceptable salt thereof; and a health functional food composition for lowering blood pressure, including Cyclo-HisPro or a sitologically acceptable salt thereof.

In addition, the present invention provides a method for lowering blood pressure, including administering Cyclo-HisPro or a pharmaceutically acceptable salt thereof to a subject in need thereof; and use of Cyclo-HisPro or a pharmaceutically acceptable salt thereof in the manufacture of an antihypertensive agent.

According to a preferred exemplary embodiment of the present invention, the Cyclo-HisPro or pharmaceutically or sitologically acceptable salt thereof may exhibit a blood pressure lowering effect in vascular endothelial cells through at least one activity selected from the group consisting of a) to e) below:

a) a decrease in the expression of angiotensin II type I receptor gene or protein;

b) an increase in the expression of angiotensin II type II receptor gene or protein;

c) an increase in the expression of VE-cadherin gene or protein;

d) an increase in the expression of eNOS gene or protein; and e) increased NO production.

According to a second aspect, the present invention provides a pharmaceutical composition for preventing or treating hypertension or a complication thereof, including Cyclo-HisPro or a pharmaceutically acceptable salt thereof; and a health functional food composition for preventing or ameliorating hypertension or a complication thereof, including Cyclo-HisPro or a sitologically acceptable salt thereof.

In addition, the present invention provides a method for preventing or treating hypertension or a complication thereof, including administering Cyclo-HisPro or a pharmaceutically acceptable salt thereof to a subject in need thereof; and use of Cyclo-HisPro or a pharmaceutically acceptable salt thereof in the manufacture of a medicament for preventing or treating hypertension or a complication thereof.

According to a preferred exemplary embodiment of the present invention, the complication may be selected from the group consisting of arteriosclerosis, coronary artery disease, myocardial infarction, heart failure, angina pectoris, peripheral blood circulation disorder, vascular stenosis, stroke, cerebral infarction, cerebral hemorrhage, ischemic brain disease, renal failure, glomerulitis, diabetes, diabetic nephropathy, diabetic retinopathy, proteinuria, uremia, edema, vision impairment due to narrowing of blood vessels in the eye and glaucoma.

Advantageous Effects

Since the composition including CHP according to the present invention exhibits a blood pressure lowering effect through a decrease in the expression of angiotensin II type I receptor gene or protein; an increase in the expression of angiotensin II type II receptor gene or protein; an increase in the expression of VE-cadherin gene or protein; an increase in the expression of eNOS gene or protein; and/or increased NO production, it is useful for the prevention, amelioration or treatment of hypertension or a complication. In addition, since it is a component derived from a natural product and is safe for the human body, it can be applied to therapeutic agents and food compositions that can replace the existing synthetic ACE inhibitors that exhibit some side effects.

BEST MODE

Figure 1:
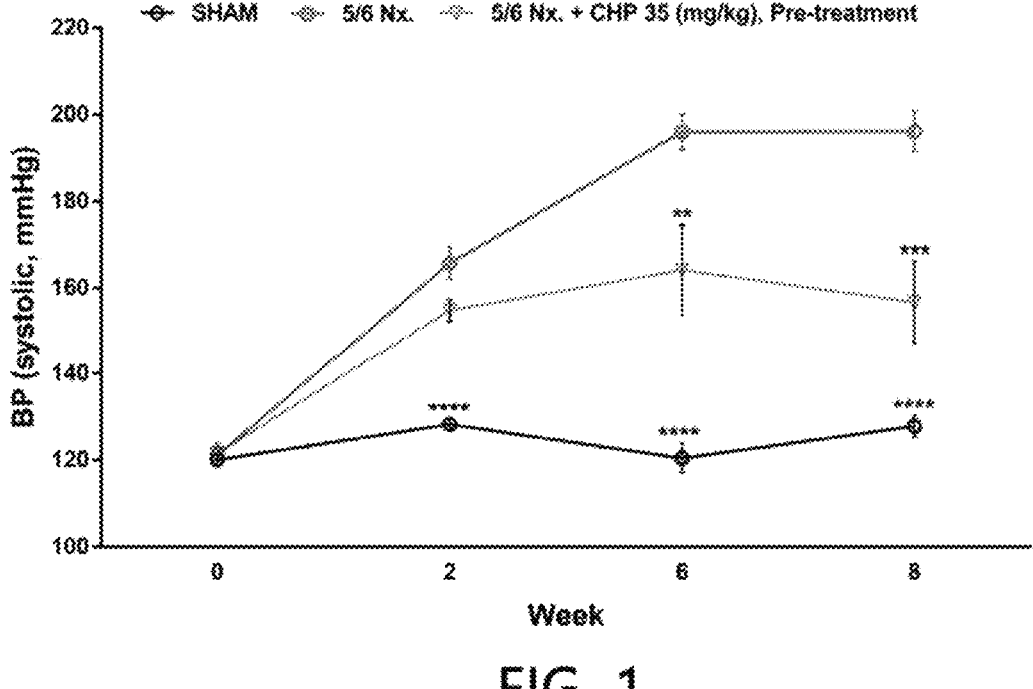
FIG. 1 is a graph showing the results of measuring systolic blood pressure at 2, 6, and 8 weeks, respectively, by administering (pre-treatment) Cyclo-HisPro 3 days before making ⅚ nephrectomy rats.

As described above, since the existing antihypertensive drugs that are manufactured through chemical synthesis methods exhibit side effects such as headache, liver disease, hot flashes, atrioventricular block and gout, attempts are being made to search for substances with a blood pressure lowering effect from natural products with few side effects and to develop the same as pharmaceuticals and food materials. Accordingly, the inventors of the present invention confirmed that Cyclo-HisPro (CHP), which is a naturally occurring circular dipeptide composed of histidine-proline that is a metabolite of thyrotropin-releasing hormone (TRH), exhibits a blood pressure lowering effect without side effects, and sought a solution to the above-described problems.

Accordingly, the first aspect of the present invention relates to a pharmaceutical composition for lowering blood pressure, including Cyclo-HisPro or a pharmaceutically acceptable salt thereof, and a health functional food composition for lowering blood pressure, including Cyclo-His-Pro or a sitologically acceptable salt thereof.

As used herein, the term "Cyclo-HisPro (CHP)" is a naturally occurring circular dipeptide composed of histi-dine-proline, which is a metabolite of thyrotropin-releasing hormone (TRH) or a physiologically active dipeptide that is also synthesized in the body de novo through the metabolic process of TRH, and it refers to a substance widely distributed in the brain, spinal cord and gastrointestinal tract.

In the composition of the present invention, the CHP may be synthesized or those that are commercially available may be used. In addition, it can be used after purification from substances containing CHP, and for example, prostate extracts and soybean hydrolyzates.

By use of the term "purified", it is intended to mean that CHP is in a concentrated form compared to a form obtain-able from a natural origin, such as prostate extracts. Purified ingredients can be concentrated from their natural sources or obtained through chemical synthesis methods.

In addition, the first aspect of the present invention relates to a method for lowering blood pressure, including administering an effective amount of Cyclo-HisPro or a pharmaceutically acceptable salt thereof to a subject in need thereof.

Additionally, the first aspect of the present invention relates to a use of Cyclo-HisPro or a pharmaceutically acceptable salt thereof in the manufacture of an antihypertensive agent.

In the first aspect of the present invention, the CHP or a pharmaceutically or sitologically salt thereof exhibits a blood pressure lowering effect in vascular endothelial cells through at least one activity selected from the group consisting of a) to e) below:

a) a decrease in the expression of angiotensin II type I receptor gene or protein;

b) an increase in the expression of angiotensin II type II receptor gene or protein;

c) an increase in the expression of VE-cadherin gene or protein;

d) an increase in the expression of eNOS gene or protein; and e) increased NO production.

Therefore, the CHP or pharmaceutically or sitologically acceptable salt thereof according to the present invention may be utilized to prevent, ameliorate or treat hypertension and/or complications thereof.

The second aspect of the present invention relates to a pharmaceutical composition for preventing or treating hypertension or a complication thereof, including Cyclo-HisPro or a pharmaceutically acceptable salt thereof, and a health functional food composition for preventing or ame-liorating hypertension or a complication thereof, including Cyclo-HisPro or a sitologically acceptable salt thereof.

Regarding the term "hypertension" of the present invention, the World Health Organization (WHO) defines hypertension as cases in which the systolic blood pressure is 160 mmHg or more and the diastolic blood pressure is 95 mmHg or more, and the type of hypertension disease is classified into essential hypertension of unknown cause and secondary hypertension caused by a causative disease, and it is known that more than 90% of hypertension pertains to essential hypertension.

As used herein, the term "complication of hypertension" may be a symptom or disease that causes hypertension, or a symptom or disease that occurs due to hypertension. Specifically, the complication of hypertension may be a symptom or disease selected from the group consisting of arteriosclerosis, coronary artery disease, myocardial infarction, heart failure, angina pectoris, peripheral blood circulation disorder, vascular stenosis, stroke, cerebral infarction, cerebral hemorrhage, ischemic brain disease, renal failure, glomerulitis, diabetes, diabetic nephropathy, diabetic retinopathy, proteinuria, uremia, edema, vision impairment due to narrowing of blood vessels in the eye and glaucoma.

In the composition for preventing, ameliorating or treating hypertension or a complication thereof according to the present invention, the terms "prevention", "amelioration" and/or "treatment" refer to any action that inhibits or delays the onset of a disease or condition, any action that ameliorates or beneficially alters a disease or condition and any action that delays, stops or reverses the progression of a disease or condition.

Figure 2:
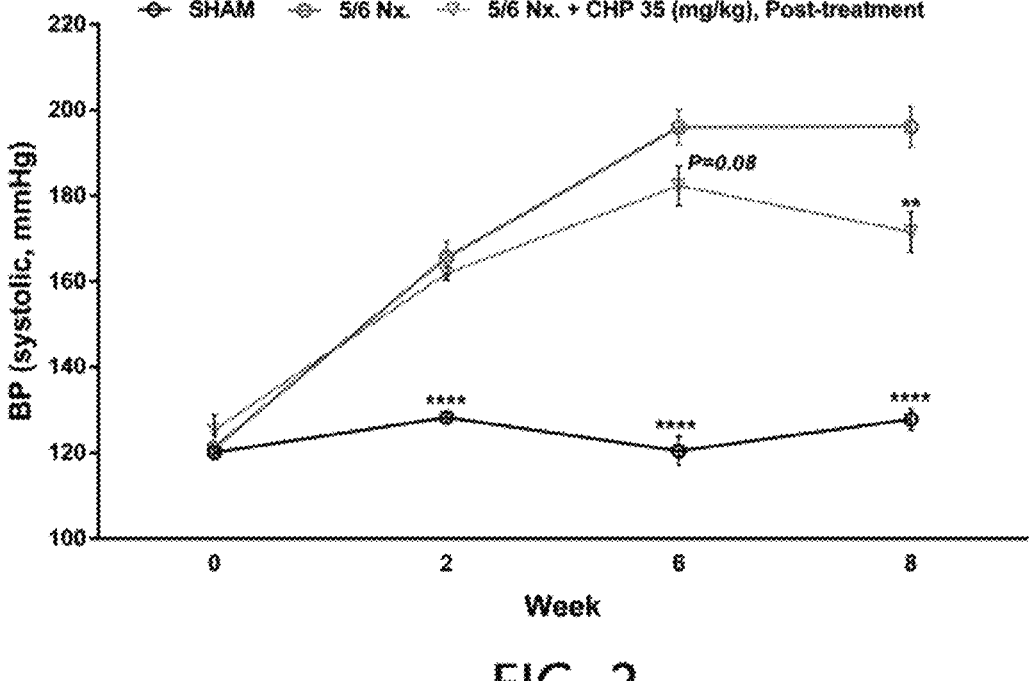
FIG. 2 is a graph showing the results of measuring systolic blood pressure at 2, 6, and 8 weeks, respectively, after administering (post-treatment) Cyclo-HisPro from 2 weeks after making ⅚ nephrectomy rats.
Figure 3A:
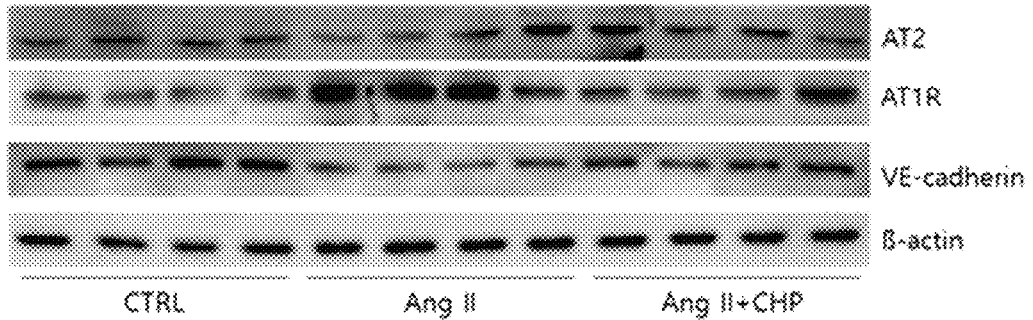
FIGS. 3A and 3B are confirmation of the expression level changes in angiotensin II type I receptor (AT1R), angiotensin II type 2 receptor (AT2R) and VE-cadherin proteins according to the treatment of angiotensin II and CHP in HUVEC cells.
Figure 3B:
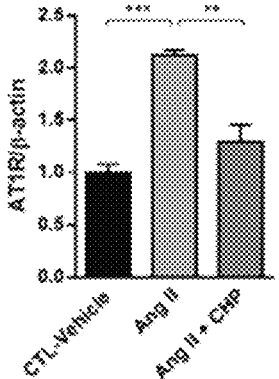
Figure 3B:
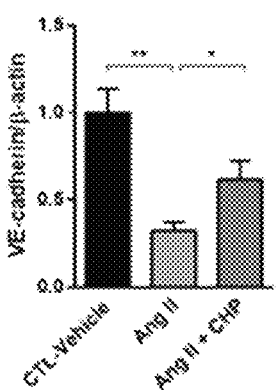
Figure 3B:
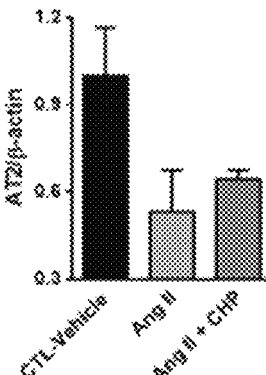

The kidney is involved in water and sodium metabolism and is closely associated with the renin-angiotensin system, and thus, kidney disease itself, that is, glomerulitis or renal failure, may cause hypertension and play an important role in the development of primary hypertension. Therefore, in an exemplary embodiment of the present invention, the CHP blood pressure lowering effect was confirmed in the nephrectomy animal model, and as shown in FIGS. 1 and 2, it was confirmed that the systolic blood pressure significantly decreased according to the CHP administration before or after the renal resection.

Therefore, the CHP of the present invention is particularly useful for the prevention, amelioration or treatment of complications related to kidney disease such as renal failure, glomerulitis, diabetic nephropathy, proteinuria or uremia.

One of the most well-known models of hypertension in cells is the angiotensin II (AngII) model. AngII binds with angiotensin receptors present in blood vessels and performs various actions, and among them, AT1 (AT1R), which is a type 1 receptor, induces vasoconstriction, and AT2 (AT2R), which is a type 2 receptor, relaxes blood vessels to perform the opposite action as AT1 (Elena Kaschina & Thomas Unger, *Blood Press,* 12 (2), 70-88, 2003). In fact, high blood pressure appears in patients with hypertension because the blood AngII concentration is maintained to be high or AT1 is expressed more strongly than AT2, and blood vessels are more likely to remain constricted rather than relaxed. Therefore, the development of drugs that reduce the expression level of AT1 or blockers that block the binding of AngII to the AT1 receptor is necessary for the development of therapeutic agents for hypertension (Le T H, et al. *Hypertension,* 42 (4), 507-514, 2003). Accordingly, in another exemplary embodiment of the present invention, the expression levels of AT1R, AT2R and VE-cadherin proteins according to the treatment of AngII and CHP in HUVEC cells were determined, and as shown in FIG. 3, CHP treatment decreased the AT1R protein expression level which was increased by AngII, increased the AT2R protein expression level which was decreased by AngII, and increased the VE-cadherin protein level which was decreased by AngII. Accordingly, it was confirmed that CHP exhibits a blood pressure lowering effect by decreasing the expression level of AT1R protein that induces vasoconstriction and increasing the expression level of AT2R protein that relaxes blood vessels.

Representative diseases caused by vasoconstriction include high blood pressure, as well as arteriosclerosis, peripheral blood circulation disorder, vascular stenosis, cerebral infarction, angina pectoris, myocardial infarction and ischemic brain disease. Vasoconstriction refers to a phenomenon in which blood vessels such as arteries including the aorta or veins are narrowed as the walls of blood vessels contract. For smooth blood circulation, an increase in blood flow in blood vessels is required, and the increase in blood flow requires the expansion of blood vessels. For vasodilation, nitric oxide (NO) is involved by the action of endothelial nitric oxide synthase (eNOS), which is a nitric oxide synthase of vascular endothelial cells (Ulrich Forstermann & Thomas Munzel, *Circulation,* 113, 1708-1714, 2006). In fact, for hypertension, NO production is reduced. In general, vascular smooth muscle is affected by several factors, and the cGMP signaling pathway of vascular smooth muscle cells by NO produced and secreted by vascular endothelial cells is a very important pathway in vascular relaxation (Zhu J, et. al., *Mol Brain,* 9, 20, 2016). NO is produced from L-arginine by eNOS in vascular endothelial cells. NO secreted from vascular endothelial cells flows into vascular smooth muscle cells, activates soluble guanylyl cyclase (sGC), and regulates blood pressure by relaxing vascular smooth muscle through a signal transduction system that increases cGMP production. Therefore, in order to treat blood pressure control disorders caused by vascular diseases, it is necessary to develop drugs that can promote NO production. Accordingly, in still another exemplary embodiment of the present invention, the eNOS gene expression level according to CHP treatment in SVEC4-10 cells and NO generation according to CHP treatment in HMVEC-L cells were determined. As a result, the eNOS gene expression level was increased by the CHP treatment as confirmed in FIG. 4, and NO production was increased by the CHP treatment as confirmed in FIG. 5. Accordingly, it was confirmed that CHP exhibits a blood pressure lowering effect by relaxing blood vessels by increasing NO production.

In addition, the second aspect of the present invention relates to a method for preventing or treating hypertension or a complication, including administering an effective amount of Cyclo-HisPro or a pharmaceutically acceptable salt thereof to a subject in need thereof.

Further, the second aspect of the present invention relates to a use of Cyclo-HisPro or a pharmaceutically acceptable salt thereof in the manufacture of a medicament for preventing or treating hypertension or a complication thereof.

As used herein, the term "pharmaceutically acceptable" means that it is physiologically acceptable and does not typically produce an allergic or similar reaction when administered to humans, and as the salt, an acid addition salt formed with a pharmaceutically acceptable free acid is preferred.

The pharmaceutically acceptable salt may be an acid addition salt formed using an organic or inorganic acid, and the organic acid includes, for example, formic acid, acetic acid, propionic acid, lactic acid, butyric acid, isobutyric acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranilic acid, dichloroacetic acid, aminooxyacetic acid, benzenesulfonic acid, p-toluenesulfonic acid or methanesulfonic acid. The inorganic acid includes, for example, hydrochloric acid, hydrobromic acid, sulfuric acid, phosphoric acid, nitric acid, carbonic acid or boric acid. The acid addition salt may preferably be in the form of a hydrochloride salt or an acetate salt, and more preferably, in the form of a hydrochloride salt.

In addition to the above, the additionally possible salt form includes a GABA salt, a gabapentin salt, a pregabalin salt, a nicotinate salt, an adipate salt, a hemimalonate, a cysteine salt, an acetylcysteine salt, a methionine salt, an arginine salt, a lysine salt, an ornithine salt, an aspartate salt or the like.

In addition, the pharmaceutical composition of the present invention may further include a pharmaceutically acceptable carrier. The pharmaceutically acceptable carrier may further include, for example, a carrier for oral administration or a carrier for parenteral administration. Carriers for oral administration may include lactose, starch, cellulose derivatives, magnesium stearate, stearic acid and the like. Carriers for parenteral administration may include water, suitable oil, saline, aqueous glucose, glycol and the like. In addition, it may further include stabilizers and preservatives. Suitable stabilizers include antioxidants such as sodium bisulfite, sodium sulfite or ascorbic acid. Suitable preservatives include benzalkonium chloride, methyl- or propyl-paraben and chlorobutanol. As other pharmaceutically acceptable carriers, reference may be made to those described in the following document (*Remington's Pharmaceutical Sciences,* 19th ed., Mack Publishing Company, Easton, Pa., 1995).

The pharmaceutical composition of the present invention may be administered in any manner to mammals, including humans. For example, it may be administered orally or parenterally, and parenteral administration may be intravenous, intramuscular, intraarterial, intramedullary, intrathecal, intracardiac, transdermal, subcutaneous, intraperitoneal, intranasal, enteral, topical, sublingual or rectal administration, but is not limited thereto.

The pharmaceutical composition of the present invention may be formulated into a preparation for oral administration or parenteral administration according to the administration route as described above. When formulated, it may be formulated with one or more buffering agents (e.g., saline or PBS), carbohydrates (e.g., glucose, mannose, sucrose, or dextran, etc.), antioxidants, bacteriostats, chelating agents (e.g., EDTA or glutathione), fillers, extenders, binders, adjuvants (e.g., aluminum hydroxide), suspending agents, thickening agents, wetting agents, disintegrating agents or surfactants, diluents or excipients.

Solid preparations for oral administration include tablets, pills, powders, granules, liquids, gels, syrups, slurries, suspensions or capsules, and such solid preparations may be prepared by mixing the pharmaceutical composition of the present invention with at least one or more excipients such as starch (including corn starch, wheat starch, rice starch, potato starch, etc.), calcium carbonate, sucrose, lactose, dextrose, sorbitol, mannitol, xylitol, erythritol, maltitol, cellulose, methyl cellulose, sodium carboxymethylcellulose, hydroxypropylmethyl-cellulose, gelatin or the like. For example, tablets or sugar tablets may be obtained by blending the active ingredient with a solid excipient, grinding it, and processing it into a granule mixture after adding suitable adjuvants.

Lubricants such as magnesium stearate talc are also used in addition to simple excipients. Liquid formulations for oral use include suspensions, solutions, emulsions, syrups or the like, and various excipients, for example, wetting agents, sweetening agents, fragrances, preservatives or the like may be included, in addition to water or liquid paraffin which are commonly used simple diluents.

Further, in some cases, cross-linked polyvinylpyrrolidone, agar, alginic acid, sodium alginate or the like may be added as a disintegrant, and an anti-aggregating agent, a lubricant, a wetting agent, a flavoring agent, an emulsifying agent, a preservative agent and the like may be further included.

For parenteral administration, the pharmaceutical composition of the present invention may be formulated in the form of an injection, a transdermal administration agent and a nasal inhalation agent together with suitable parenteral carriers according to methods known in the art. The injection must be sterilized and protected from contamination of microorganisms such as bacteria and fungi. Examples of suitable carriers for injection may be solvents or dispersion media including water, ethanol, polyols (e.g., glycerol, propylene glycol, liquid polyethylene glycol, etc.), mixtures thereof and/or vegetable oils, but are not limited thereto. More preferably, as suitable carriers, Hanks' solution, Ringer's solution, phosphate buffered saline (PBS) containing triethanolamine or isotonic solutions such as sterile water for injection, 10% ethanol, 40% propylene glycol, 5% dextrose and the like may be used. In order to protect the injection from microbial contamination, various antibacterial and antifungal agents such as paraben, chlorobutanol, phenol, sorbic acid, thimerosal and the like may be further included. In addition, in most cases, the injection may further include isotonic agents such as sugar or sodium chloride.

In the case of transdermal administration agents, forms such as an ointment, cream, lotion, gel, an external solution, a paste preparation, a liniment, aerosol and the like are included. In the above, the term 'transdermal administration' means that an effective amount of the active ingredient contained in the pharmaceutical composition is delivered into the skin by topically administering the pharmaceutical composition to the skin.

In the case of inhalation administration agents, the compound used in accordance with the present invention may be conveniently delivered in the form of an aerosol spray from a pressurized pack or a nebulizer, with the use of a suitable propellant such as dichlorofluoromethane, trichlorofluoromethane, dichlorotetrafluoroethane, carbon dioxide or other suitable gas. In the case of a pressurized aerosol, the dosage unit may be determined by providing a valve to deliver a measured amount. For example, gelatin capsules and cartridges used in inhalers or insufflators may be formulated to contain a powder mixture of the compound and a suitable powder base such as lactose or starch. Formulations for parenteral administration are described in the following document which is a commonly known prescription in all of pharmaceutical chemistry (*Remingion's Pharmaceutical Science,* 15th Edition, 1975. Mack Publishing Company, Easton, Pa. 18042, Chapter 87: Blaug, Seymour).

When the pharmaceutical composition of the present invention includes Cyclo-HisPro in an effective amount, it is possible to provide desirable effects of lowering blood pressure or preventing, ameliorating or treating hypertension or a complication thereof. As used herein, the term "effective amount" refers to an amount that exhibits a response greater than that of a negative control group, and preferably refers to an amount sufficient to prevent, ameliorate or treat hypertension or a complication. The pharmaceutical composition of the present invention may include 0.01 to 99.9% of Cyclo-HisPro, and the remaining amount may be occupied by a pharmaceutically acceptable carrier. The effective amount of Cyclo-HisPro included in the pharmaceutical composition of the present invention may vary depending on the form in which the composition is commercialized.

The total effective amount of the pharmaceutical composition of the present invention may be administered to a patient in a single dose, or may also be administered by a fractionated treatment protocol in which multiple doses are administered over a long period of time. The pharmaceutical composition of the present invention may have a varied content of the active ingredient depending on the severity of the disease. For example, it may be administered in a single dose to several divided doses such that it is preferably administered in an amount of 0.001 to 100 mg/kg of body weight per day or more preferably, 0.01 to 10 mg/kg of body weight per day, based on Cyclo-HisPro. However, for the dose of Cyclo-HisPro, the effective dose for a patient is determined by considering various factors such as the patient's age, body weight, health status, gender, severity of the disease, diet and excretion rate, as well as the route of administration and number of treatments of the pharmaceutical composition, and thus, one of ordinary skill in the art will be able to determine the appropriate effective dose of the Cyclo-HisPro according to the particular use for lowering blood pressure, or for preventing, treating or ameliorating hypertension or a complication thereof. The pharmaceutical composition according to the present invention is not particularly limited in its formulation, administration route and administration method as long as it shows the effects of the present invention.

The pharmaceutical composition of the present invention may be used alone or in combination with methods using surgery, radiation therapy, hormone therapy, chemotherapy or a biological response modifier.

The pharmaceutical composition of the present invention may also be provided as a formulation for an external preparation including Cyclo-HisPro. In this aspect, the composition of the present invention may be a quasi-drug composition for lowering blood pressure, or preventing or ameliorating hypertension or a complication thereof, and a quasi-drug including the composition.

The external preparation may be applied directly to the skin. When the pharmaceutical composition of the present invention is used as an external preparation, the pharmaceutical composition may further include adjuvants generally used in the field of dermatology, such as any other components generally used in the preparation for external use on skin, for example, a fatty material, an organic solvent, a dissolving agent, concentrating and gelling agents, a softening agent, an antioxidant, a suspending agent, a stabilizing agent, a foaming agent, a flavoring agent, a surfactant, water, an ionic emulsifying agent, a non-ionic emulsifying agent, a filler, a sequestering agent, a chelating agent, a preservative, a vitamin, a blocking agent, a wetting agent, an essential oil, a dye, a pigment, a hydrophilic activating agent, a hydrophobic activating agent, or a lipid vesicle. In addition, the components may be introduced at an amount generally used in the field of dermatology.

When the pharmaceutical composition of the present invention is provided as an external preparation, it may be provided as a formation of a liquid, an ointment, a patch, a gel, a cream or a spray, but the present invention is not limited thereto. According to an embodiment of the present invention, the quasi-drug of the present invention may include an ointment, a mask, a poultice, a patch and a transdermal absorbent.

When the pharmaceutical composition of the present invention is used as a quasi-drug composition, Cyclo-HisPro may be added as it is or may be appropriately used in combination with other quasi-drug ingredients according to a conventional method. The mixing amount of the active ingredient may be appropriately determined according to the purpose of use (prevention, health or therapeutic treatment).

The contents of the pharmaceutical composition and health functional food composition of the present invention may be applied mutatis mutandis to the quasi-drug composition and quasi-drug of the present invention.

As used herein, the term "health functional food" includes both the meanings of "functional food" and "health food."

As used herein, the term "functional food" is the same term as food for special health use (FoSHU), and means a food product with high medicinal and medical effects, which is processed to efficiently exhibit bioregulatory functions in addition to nutrition supply.

As used herein, the term "health food" refers to food having an active health maintenance or effect as compared with general food, and health supplement food refers to food for the purpose of health supplementation. In some cases, the terms of functional food, health food and health functional food are interchangeably used. The food may be prepared in various forms such as tablets, capsules, powders, granules, liquids, pills and the like.

As a specific example of such functional food, by using the composition, it is possible to produce processed food with improved storage properties while modifying to take into account the characteristics of agricultural products, livestock products or aquatic products.

The health functional food composition of the present invention may also be prepared in the form of nutritional supplements, food additives and feed, and it is intended for consumption by animals, including humans or livestock.

This type of food compositions may be prepared in various forms according to conventional methods known in the art. As general food, Cyclo-HisPro may be added to produce beverages (including alcoholic beverages), fruits and processed food thereof (e.g., canned fruit, bottled fruit, jam, marmalade, etc.), fish, meat and processed food thereof (e.g., ham, sausages, corn beef, etc.), breads and noodles (e.g., udon noodles, soba noodles, ramen, spaghetti, macaroni, etc.), fruit juice, various drinks, cookies, Korean hard taffy, dairy products (e.g., butter, cheese, etc.), edible vegetable oils and fats, margarine, vegetable proteins, retort food, frozen food, various seasonings (e.g., soybean paste, soy sauce, sauce, etc.) and the like, but the present invention is not limited thereto.

In addition, as nutritional supplements, Cyclo-HisPro may be added to produce capsules, tablets, pills and the like, but the present invention is not limited thereto.

In addition, as health functional food, for example, the Cyclo-HisPro may be prepared in the form of tea, juice and drink and consumed by liquefying, granulating, encapsulating and powdering such that it may be ingested (health drink), but the present invention is not limited thereto. Further, in order to use the Cyclo-HisPro in the form of food additives, it may be prepared and used in the form of powder or a concentrate. In addition, the Cyclo-HisPro may be mixed with a known active ingredient known to be effective in preventing or ameliorating hypertension or a complication thereof, and prepared in the form of a composition.

When the food composition of the present invention is used as a health beverage composition, the health beverage composition may contain various flavoring agents, natural carbohydrates or the like as additional components, as in conventional beverages. The aforementioned natural carbohydrates may be monosaccharides such as glucose and fructose; disaccharides such as maltose and sucrose; polysaccharides such as dextrin and cyclodextrin; sugar alcohols such as xylitol, sorbitol, erythritol and the like. As sweetening agents, natural sweetening agents such as thaumatin and stevia extract; synthetic sweeteners such as saccharin, aspartame and the like may be used. The proportion of such natural carbohydrates is generally about 0.01 to 0.04 g, preferably about 0.02 to 0.03 g per 100 mL of the composition of the present invention.

Cyclo-HisPro may be contained as an active ingredient in a food composition for lowering blood pressure, or preventing or ameliorating hypertension or a complication thereof, and the amount is an effective amount to obtain the preventive or ameliorating effect, and for example, it is preferably 0.01 to 100% by weight based on the total weight of the total composition, but the present invention is not particularly limited thereto. The food composition of the present invention may be prepared by mixing with Cyclo-HisPro with other active ingredients known to be effective in lowering blood pressure, or preventing or ameliorating hypertension or a complication thereof.

In addition to the above, the health functional food of the present invention may contain various nutrients, vitamins, electrolytes, flavoring agents, coloring agents, pectic acid, salts of pectic acid, alginic acid, salts of alginic acid, organic acids, protective colloid thickeners, pH regulators, stabilizers, antiseptics, glycerin, alcohols, carbonating agents or the like. In addition, the health food of the present invention may contain fruit flesh for the production of natural fruit juice, fruit juice beverages, or vegetable beverages. These components may be used independently or in combination. The proportion of these additives is not critically important, but is generally chosen in a range from 0.01 to 0.1 parts by weight per 100 parts by weight of the composition of the present invention.

In the method of the present invention, the term "subject" includes any animal (e.g., human, horse, pig, rabbit, dog, sheep, goat, non-human primate, cow, cat, guinea pig or rodent), but is not limited thereto. These terms do not denote a specific age or gender. Accordingly, these are intended to include adult/adult and neonatal subjects, whether female/female or male/male, as well as fetuses. A patient refers to a subject afflicted with a disease or disorder. The term "patient" includes human and veterinary subjects.

In the method of the present invention, the description of the composition including the effect of CHP and the administration route thereof, the number of administrations, the dosage and the like is the same as described above, and thus, the description thereof will be omitted.

Hereinafter, the present invention will be described in more detail through examples. However, since the present invention may have various changes and forms, the specific examples and descriptions described below are only for helping the understanding of the present invention and are not intended to limit the present invention to a specific disclosed form. It should be understood that the scope of the present invention includes all modifications, equivalents and substitutes included in the spirit and scope of the present invention.

MODES OF THE INVENTION

Preparation Example

Cyclo-HisPro (CHP) used in the following examples was purchased from Bachem and used.

Example 1

Measurement of Prophylactic Effect of Blood Pressure Control in Rats by Cyclo-HisPro Treatment
1-1. Construction of 5/6 Nephrectomy Model and Cyclo-HisPro Administration The kidney is involved in water and sodium metabolism and is closely associated with the renin-angiotensin system, and thus, kidney disease itself, that is, glomerulitis or renal failure, may cause hypertension and play an important role in the development of essential hypertension. Chronic renal failure through nephrectomy in rats leads to continued progression of hypertension, uremia, proteinuria and glomerulosclerosis.

After pre-bringing 7-week-old SD rats purchased from Koatech Co., Ltd. for more than one week, the experimental group underwent surgery in two stages. After general anesthesia, incision was performed along the midline of the abdomen to separate the left kidney from the adrenal glands and surrounding tissues, and after holding the renal blood vessel with forceps to prevent bleeding, the upper 1/3 and lower 1/3 of the left kidney were removed, and after 1 week, general anesthesia was performed again, and the entire right kidney was removed to complete a 5/6 nephrectomy model.

The rats were divided into 3 groups of 8 animals, the first group was set as a normal control group (SHAM) without nephrectomy and administered with phosphate buffered saline, the second group was set as a disease control group which underwent 5/6 nephrectomy (5/6 Nx.) and was not administered with Cyclo-HisPro but administered with phosphate buffered saline, and the third group was orally administered with Cyclo-HisPro at 35 mg/kg every other day for 8 weeks from 3 days before nephrectomy.
1-2. Measurement of Blood Pressure in Rats In order to reduce the error range of blood pressure measurement, the experimental animals were calibrated in the holder of a blood pressure meter (BP-2000 blood pressure analysis system, rat platform 2-channel, Visitech Systems, Apex, NC, USA) and then acclimatized in a heating chamber at 37° C. for 30 minutes, and the systolic blood pressure was measured at least 5 times in the tail artery to obtain the average value. The significance of the experimental results was verified by performing t-test for each group of the disease control group (Nx), the normal control group and the Cyclo-HisPro administration group, and there was a statistically significant difference ($p < 0.005$, *$p < 0.0005$, ****$p < 0.00005$).

As a result, as shown in FIG. 1, it could be observed that the systolic blood pressure of the disease control group (Nx) significantly increased in a time-dependent manner compared to the normal control group (SHAM). On the other hand, in the group administered with Cyclo-HisPro, it was confirmed that the systolic blood pressure was significantly reduced than that of the disease control group (Nx). Specifically, the systolic blood pressure of the normal control group (SHAM) was 127.8 mmHg and the systolic blood pressure of the disease control group (Nx) was 196.2 mmHg, but the systolic blood pressure of the group administered with Cyclo-HisPro was 156.7 mmHg Therefore, it was confirmed that administration of Cyclo-HisPro had a prophylactic effect on lowering blood pressure.

Example 2

Measurement of Therapeutic Effect of Blood Pressure Control in Rats by Cyclo-HisPro
2-1. Construction of 5/6 Nephrectomy Model and Administration of Cyclo-HisPro A 5/6 nephrectomy model was constructed in the same manner as in Example 1-1, and the rats were divided into 3 groups of 8 animals. The first and second groups were treated in the same way, but the third group was orally administered with Cyclo-Hispro at 35 mg/kg every other day for 6 weeks from 2 weeks after nephrectomy.
2-2. Measurement of Blood Pressure in Rats As a result of measuring the blood pressure of the rats of each group in the same manner as in Example 1-2, it could be observed that the systolic blood pressure of the disease control group (Nx) significantly increased in a time-dependent manner compared to the normal control group (SHAM) as shown in FIG. 2. On the other hand, it was confirmed that the systolic blood pressure in the group administered with Cyclo-HisPro was significantly reduced than that of the disease control group (Nx). Specifically, the systolic blood pressure of the normal control group (SHAM) was 127.8 mmHg and the systolic blood pressure of the disease control group (Nx) was 196.2 mmHg, but the systolic blood pressure of the group administered with Cyclo-HisPro was 171.6 mmHg Therefore, it was confirmed that the administration of Cyclo-HisPro had a therapeutic effect on blood pressure control.

Example 3

Confirmation of Expressions of AT1R, AT2R and VE-Cadherin Proteins According to Treatments of Angiotensin II and CHP in HUVEC Cells
3-1. HUVEC Cell Culture Human umbilical vein endothelial cells (HUVEC, CRL-1730) were obtained from the American Type Culture Collection (ATCC), and EBM-2 basal medium and EGM-2 MV microvascular endothelial cell growth medium SingleQuots supplements were purchased from Lonza.

HUVEC cells were cultured in EBM-2 medium supplemented with EGM-2 MV SingleQuots supplements at 37° C. and 5% $CO_2$ conditions. The medium was replaced every 2 to 3 days, and subculture was performed at 70 to 80% confluency.
3-2. Confirmation of Expression Levels of AT1R, AT2R and VE-Cadherin Proteins HUVEC cells were divided into three groups and treated as shown in Table 1.

TABLE 1

| Group | Treatment |
| --- | --- |
| Normal control group (control) | Vehicle |
| Positive control group | Ang II |
| CHP treatment group | Ang II and CHP |

HUVEC cells treated with angiotensin II and CHP were placed in 500 uL of RIPA buffer containing protease and phosphatase inhibitors, and then pulverized by using IKA's T10 homogenizer. After standing on ice for 15 minutes, centrifugation was performed at 15,000 rpm at 4° C. The supernatant was collected and the protein concentration was measured by BCA quantitation, and the same amount of samples was separated by using the Bolt TM protein gel electrophoresis system, and then transferred to a nitrocellulose membrane. The membrane was blocked with 5% skim milk at room temperature for 1 hour, and then it was reacted with the primary antibodies, AT1R (angiotensin II type I receptor), AT2R (angiotensin II type 2 receptor), VE-cadherin and β-actin antibody, overnight at 4° C. After washing 3 times for 10 minutes with TBST, the reaction was performed with the secondary antibody at room temperature for 1 hour. After washing 3 times for 10 minutes with TBST, the expression level was measured by reacting with ECL. The size of the appearing band was quantified by using the ImageJ program and corrected by dividing the size value of each band by the size value of the β-actin band. Statistical significance was analyzed by using Student's t-test statistical method with angiotensin II-treated control group (Ang II) (*$p<0.05$, $p<0.05$, *$p<0.0005$).

As a result of the experiment, as shown in FIG. 3, the protein expression of AT1 (AT1R), which induces vasoconstriction, increased according to the treatment of angiotensin II (AngII) in HUVEC cells, and the protein expression of AT2 (AT2R), which acts opposite to AT1 by relaxing blood vessels, was reduced. In the CHP-treated group, it was confirmed that AT1R was statistically significantly decreased and AT2 tended to increase. In addition, although VE-cadherin, which plays an important role in angiogenesis, was decreased by the treatment of angiotensin II (AngII), it was confirmed that the expression of VE-cadherin protein was statistically significantly increased in the group treated with CHP.

Through the results of the present example, it was confirmed that CHP decreases the expression of angiotensin II receptor 1 (AT1R), which induces vasoconstriction, and increases the expression of angiotensin II receptor 2 (AT2R), which relaxes blood vessels, thereby exhibiting a blood pressure lowering effect, and it sufficiently proves that CHP can be applied to the treatment of hypertension.

Example 4

Confirmation of eNOS Gene Expression According to CHP Treatment in SVEC4-10 Cells 4-1. SVEC4-10 Cell Culture SVEC4-10 (CRL-2181), which is a mouse endothelial cell line, was obtained from the American Type Culture Collection (ATCC), and RPMI-1640 medium and FBS were purchased from Hyclone.

SVEC4-10 cells were cultured at 37° C. and 5% $CO_2$ conditions by using RPMI-1640 medium containing 10% FBS and 1% penicillin/streptomycin, and subculture was performed every 2 days.

4-2. Confirmation of eNOS Gene Expression Level

SVEC4-10 cells were placed in a 6-well plate at $5\times10^5$ cells and cultured for 24 hours. CHP was treated at concentrations of 0, 10, 100 and 250 μM in serum-free medium, respectively, and then it was cultured at 37° C. and 5% $CO_2$ conditions for 2 hours. Thereafter, the medium was removed, and it was washed once with cold PBS and then immediately dissolved using NucleoZOL.

For RNA extraction, RNA was extracted according to the manufacturer's total RNA isolation protocol by using NucleoZOL (MACHEREY-NAGEL), and 1 μg of RNA was subjected to reverse transcription polymerase chain reaction to synthesize cDNA by using iScript cDNA synthesis kit (Bio-Rad). The synthesized cDNA was analyzed by real-time PCR using iQ SYBR Green Supermix (Bio-Rad) by using the primer set of the eNOS gene. In this case, the primer set used was used by requesting synthesis from Bioneer with the nucleotide sequences shown in Table 2.

TABLE 2

| Gene | Forward primer (5'→3') | SEQ ID NO: | Reverse primer (5'→3') | SEQ ID NO: |
| --- | --- | --- | --- | --- |
| eNOS | CCCGGAAAGAGGGA TTGTGT | 1 | TGCAACCAATGCTG TAGGCA | 2 |
| β-actin | GGGAAGGTGACAGC ATTG | 3 | ATGAAGTATTAAGG CGGAAGATT | 4 |

Each gene expression value was corrected by dividing by the expression value of β-actin, which is a housekeeping gene. Statistical significance was analyzed by the Student's t-test statistical method (*$p<0.05$).

Figure 4:
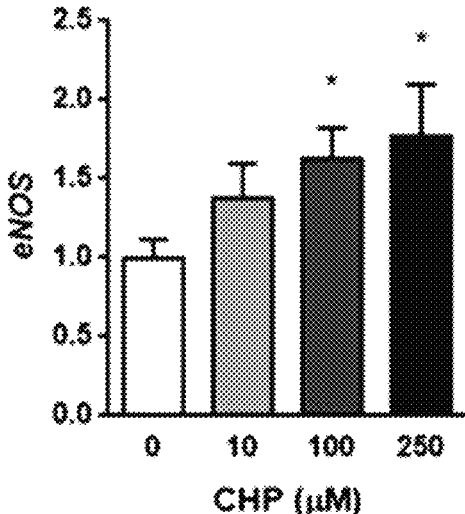
FIG. 4 is a graph showing that the expression of the eNOS gene in SVEC4-10 cells increased in a CHP concentration-dependent manner.

As a result of the experiment, as shown in FIG. 4, it was confirmed that the expression of the eNOS gene for producing nitric oxide significantly increased according to the CHP treatment. Due to this, it was expected that nitric oxide production would be promoted, blood vessels would be relaxed and blood pressure would be effectively controlled.

Example 5

Confirmation of NO Production According to CHP Treatment in HMVEC-L Cells 5-1. HMVEC-L Cell Culture Human lung microvascular cells (HMVEC-L, CC2527) were obtained from the American Type Culture Collection (ATCC), and EBM-2 basal medium and EGM-2 MV microvascular endothelial cell growth medium SingleQuots supplements were purchased from Lonza.

HUVEC-L cells were cultured in EBM-2 medium supplemented with EGM-2 MV SingleQuots at 37° C. and 5% $CO_2$ conditions. The medium was replaced every 2 to 3 days, and subculture was performed at 70 to 80% confluency.

5-2. Confirmation of NO Production $5\times10^4$ cells were placed in a black 96-well plate, incubated for 24 hours and treated with CHP at concentrations of 0, 1, 10, 100 and 500 μM in serum-free medium, respectively, and cultured at 37° C. and 5% $CO_2$ conditions for 2 hours. DAF-FM DA (DAF-FM Diacetate; Invitrogen) at a concentration of 5 μM was added and further incubated for 30 minutes, and it was washed once with PBS and observed with a fluorescence microscope at FITC wavelength. Photographs were taken at the same exposure time, and the fluorescence intensity of each cell was measured by using the ImageJ tool. Statistical significance was analyzed by one-way ANOVA statistical method, and comparison with the control group which was not treated with CHP was analyzed by Dunnett's test (****p<0.0001).

Figure 5A:
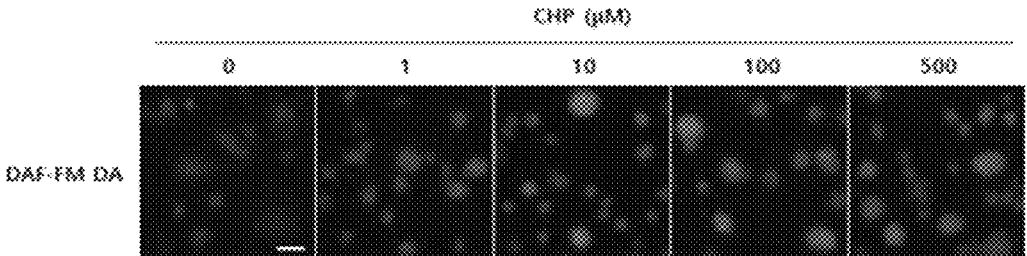
FIGS. 5A and 5B are confirmation of increased NO production according to the treatment of CHP in HMVEC-L cells by using DAF-FM DA (scale bar 50 μm).
Figure 5B:
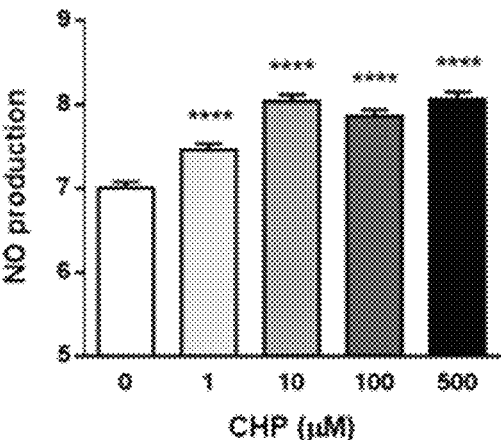

As a result of the experiment, as shown in FIG. 5, it was confirmed that the intensity of DAF-FM DA fluorescence in HMVEC-L cells increased as the CHP was treated. Since the intensity of fluorescence reflects the amount of intracellular NO, it can be seen that NO production in vascular endothelial cells was significantly increased by CHP treatment.

NO production in vascular endothelial cells promotes the relaxation of vascular smooth muscle cells, thereby lowering blood pressure along with vascular relaxation. Therefore, it was confirmed through the results of the present example that CHP can improve the blood pressure control function by increasing NO production.

Statistical Analysis of Results

Statistical significance was analyzed by using Student's t-test and one-way ANOVA statistical methods, and outliers were analyzed by using GraphPad's Grubb's Outlier calculator. Significant outliers were excluded from the summation of results.

The invention claimed is:

1. A method for lowering blood pressure by relaxing blood vessels in a subject having essential hypertension or secondary hypertension caused by kidney disease or diabetes, comprising administering a composition consisting of an effective amount of Cyclo-HisPro or a pharmaceutically acceptable salt thereof as a sole active ingredient, or an effective amount of Cyclo-HisPro or a pharmaceutically acceptable salt thereof as a sole active ingredient and a pharmaceutically acceptable carrier to the subject.

2. The method of claim 1, wherein the Cyclo-HisPro or pharmaceutically acceptable salt thereof exhibits a blood pressure lowering effect in vascular endothelial cells through at least one activity selected from the group consisting of a) to e) below:

a) a decrease in the expression of angiotensin II type I receptor gene or protein;
  b) an increase in the expression of angiotensin II type II receptor gene or protein;
  c) an increase in the expression of VE-cadherin gene or protein;

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: eNOS forward primer

<400> SEQUENCE: 1
cccggaaaga gggattgtgt                                          20

<210> SEQ ID NO 2
<211> LENGTH: 20
<212> TYPE: DNA
<213> ORGANISM: Artificial
<220> FEATURE:
<223> OTHER INFORMATION: eNOS reverse primer

<400> SEQUENCE: 2
tgcaaccaat gctgtaggca                                          20

<210> SEQ ID NO 3
<211> LENGTH: 18
<212> TYPE: DNA
<213> ORGANISM: Artificial
<220> FEATURE:
<223> OTHER INFORMATION: Beta-actin forward primer

<400> SEQUENCE: 3
gggaaggtga cagcattg                                            18

<210> SEQ ID NO 4
<211> LENGTH: 23
<212> TYPE: DNA
<213> ORGANISM: Artificial
<220> FEATURE:
<223> OTHER INFORMATION: Beta-actin reverse primer

<400> SEQUENCE: 4
atgaagtatt aaggcggaag att                                      23
``` d) an increase in the expression of eNOS gene or protein; and e) increased NO production.

3. A method for treating hypertension by relaxing blood vessels in a subject having essential hypertension or secondary hypertension caused by kidney disease or diabetes, comprising administering a composition consisting of an effective amount of Cyclo-HisPro or a pharmaceutically acceptable salt thereof as a sole active ingredient, or an effective amount of Cyclo-HisPro or a pharmaceutically acceptable salt thereof as a sole active ingredient and a pharmaceutically acceptable carrier to the subject.

\* \* \* \* \*